(12) United States Patent
Hammon et al.

(10) Patent No.: US 10,413,841 B2
(45) Date of Patent: Sep. 17, 2019

(54) COLUMN FOR THERMAL TREATMENT OF FLUID MIXTURES

(71) Applicant: BASF SE, Ludwigshafen (DE)

(72) Inventors: Ulrich Hammon, Mannheim (DE); Thomas Walter, Hassloch (DE)

(73) Assignee: BASF SE, Ludwigshafen (DE)

( * ) Notice: Subject to any disclaimer, the term of this patent is extended or adjusted under 35 U.S.C. 154(b) by 132 days.

(21) Appl. No.: 14/816,485

(22) Filed: Aug. 3, 2015

(65) Prior Publication Data

US 2016/0038852 A1 Feb. 11, 2016

Related U.S. Application Data

(60) Provisional application No. 62/033,173, filed on Aug. 5, 2014.

(30) Foreign Application Priority Data

Aug. 5, 2014 (DE) .................. 10 2014 215 438

(51) Int. Cl.
*B01D 3/32* (2006.01)
*B01D 3/26* (2006.01)
*C07C 51/44* (2006.01)

(52) U.S. Cl.
CPC .............. *B01D 3/326* (2013.01); *B01D 3/26* (2013.01); *B01D 3/324* (2013.01); *C07C 51/44* (2013.01)

(58) Field of Classification Search
CPC .......... B01D 3/326; B01D 3/324; B01D 3/26; C07C 51/44
See application file for complete search history.

(56) References Cited

U.S. PATENT DOCUMENTS

| | | | | |
|---|---|---|---|---|
| 2,710,678 A | * | 6/1955 | Rapisarda | B01D 3/326 24/571 |
| 2,711,307 A | * | 6/1955 | Milmore | B01D 3/18 261/108 |
| 3,632,315 A | * | 1/1972 | Uitti | B01D 11/043 422/256 |
| 3,642,258 A | * | 2/1972 | Stahl | B01D 3/326 261/113 |

(Continued)

FOREIGN PATENT DOCUMENTS

| | | | | |
|---|---|---|---|---|
| CA | 2814848 A1 | * | 5/2012 | ............ B01D 3/008 |
| DE | 216 633 A1 | | 12/1984 | |

(Continued)

*Primary Examiner* — Stephen Hobson
(74) *Attorney, Agent, or Firm* — Oblon, McClelland, Maier & Neustadt, L.L.P.

(57) ABSTRACT

The present invention relates to a column (1) for thermal treatment of fluid mixtures, having a cylindrical, vertical column body (2) which forms a column cavity (3), a plurality of trays (8) mounted with vertical spacing in the column cavity (3), and a support construction (9) which supports at least one of the trays (8) in vertical direction. It is a characteristic feature of the inventive column (1) that the support construction (9) has a plurality of orifices (12) which allow horizontal mass transfer through the support construction (9). The invention further relates to a tray device for such a column and to a thermal separation process between at least one gas ascending within such a column (1) and at least one liquid descending within the column (1).

14 Claims, 5 Drawing Sheets

(56) References Cited

U.S. PATENT DOCUMENTS

Figure 1:
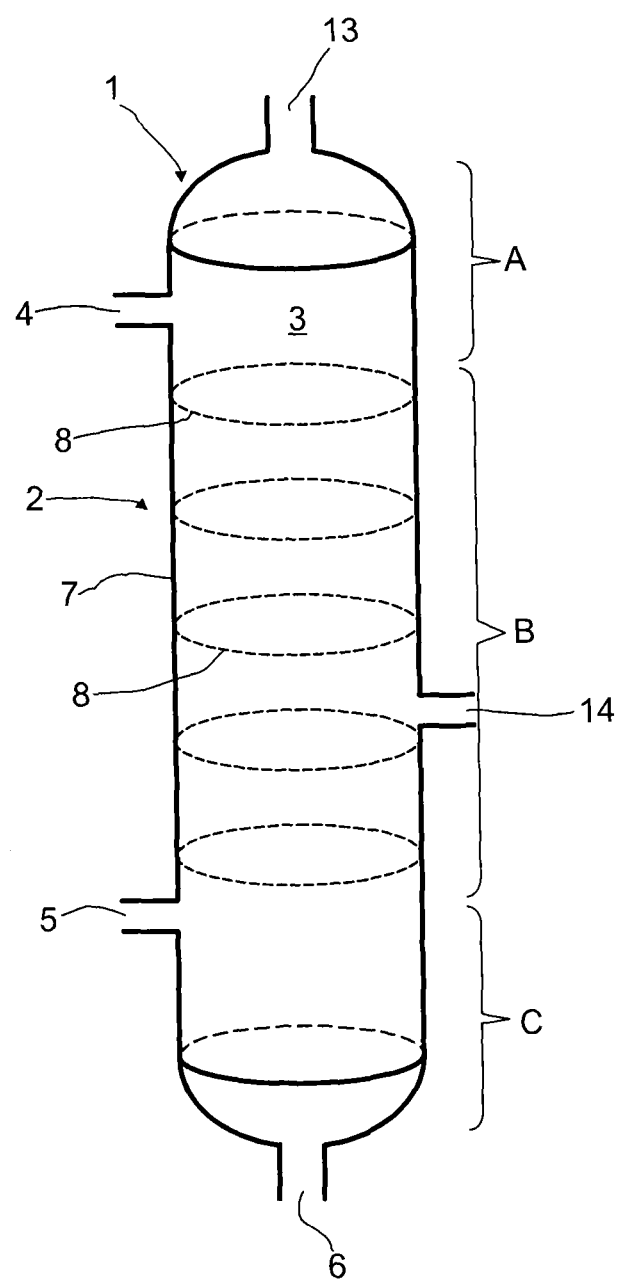

| | | | |
|---|---|---|---|
| 3,988,213 A | 10/1976 | Yoshida et al. | |
| 5,788,895 A * | 8/1998 | Altinger | B01D 3/324 261/113 |
| 6,131,891 A * | 10/2000 | Resetarits | B01D 3/20 202/158 |
| 6,423,235 B1 * | 7/2002 | Shimoi | B01D 19/0015 210/760 |
| 6,962,661 B2 * | 11/2005 | Northup, Jr. | B01D 11/043 196/14.52 |
| 7,235,158 B2 * | 6/2007 | Matsumoto | B01D 3/22 202/158 |
| 7,288,169 B2 * | 10/2007 | Yada | B01D 3/10 202/158 |
| 7,810,796 B2 * | 10/2010 | Xu | B01D 3/326 261/114.1 |
| 2004/0206617 A1 * | 10/2004 | Diehl | B01D 3/324 203/8 |
| 2005/0218534 A1 * | 10/2005 | Colic | B01D 3/20 261/114.5 |
| 2008/0183014 A1 * | 7/2008 | Diefenbacher | C07C 51/44 562/600 |
| 2011/0240458 A1 * | 10/2011 | Cartage | B01D 3/20 203/49 |
| 2012/0111717 A1 | 5/2012 | Headley et al. | |
| 2012/0228251 A1 * | 9/2012 | Headley | B01D 3/326 211/124 |
| 2012/0292791 A1 * | 11/2012 | Headley | B01D 3/225 261/114.1 |
| 2018/0178172 A1 * | 6/2018 | Nieuwoudt | B01F 3/04078 |
| 2019/0046894 A1 * | 2/2019 | Headley | B01D 3/326 |

FOREIGN PATENT DOCUMENTS

| | | |
|---|---|---|
| DE | 279 822 A1 | 6/1990 |
| DE | 197 40 252 A1 | 3/1999 |
| DE | 197 40 253 A1 | 3/1999 |
| DE | 199 24 532 A1 | 11/2000 |
| DE | 199 24 533 A1 | 11/2000 |
| DE | 101 56 988 A1 | 5/2003 |
| DE | 101 59 823 A1 | 6/2003 |
| DE | 102 18 419 A1 | 6/2003 |
| DE | 102 57 916 A1 | 10/2003 |
| DE | 102 30 219 A1 | 1/2004 |
| DE | 103 36 386 A1 | 3/2004 |
| DE | 102 43 625 A1 | 4/2004 |
| DE | 103 32 758 A1 | 5/2004 |
| DE | 10 2010 001 228 A1 | 2/2011 |
| EP | 0 700 714 A1 | 3/1996 |
| EP | 0 700 893 A1 | 3/1996 |
| EP | 0 882 481 A1 | 12/1998 |
| EP | 0 982 287 A1 | 3/2000 |
| EP | 0 982 289 A2 | 3/2000 |
| EP | 1 029 573 A2 | 8/2000 |
| EP | 1 125 912 A2 | 8/2001 |
| EP | 1 279 429 A1 | 1/2003 |
| EP | 1 704 906 A1 | 9/2006 |
| WO | WO 2004/035514 A1 | 4/2004 |
| WO | WO 2004/092108 A1 | 10/2004 |
| WO | WO 2008/090190 A1 | 7/2008 |
| WO | WO-2013138185 A1 * | 9/2013 ............ B01D 3/225 |

\* cited by examiner

COLUMN FOR THERMAL TREATMENT OF FLUID MIXTURES

The present invention relates to a column for thermal treatment of fluid mixtures. It has a cylindrical, vertical column body which forms a column cavity. The column further comprises a plurality of trays mounted with vertical spacing in the column cavity. In addition, the column has a support construction which supports at least one of the trays in vertical direction. The column is especially a separating column. The invention further relates to a tray device for such a column and to a thermal separation process between at least one gas ascending within a column and at least one liquid descending within the column.

In separating columns, gaseous (ascending) and liquid (descending) streams are in many cases conducted in countercurrent, at least one of the streams especially comprising a (meth)acrylic monomer. As a result of the inequilibria that exist between the streams, heat and mass transfer takes place, which ultimately causes the removal (or separation) desired in the separating column. In this document, such separating processes shall be referred to as thermal separating processes.

Examples of, and hence elements of, the expression "thermal separating processes" used in this document are fractional condensation (cf., for example, DE 19924532 A1, DE 10243625 A1 and WO 2008/090190 A1) and rectification (in both cases, ascending vapor phase is conducted in countercurrent to descending liquid phase; the separating action is based on the vapor composition at equilibrium being different from the liquid composition), absorption (at least one ascending gas is conducted in countercurrent to at least one descending liquid; the separating action is based on the different solubility of the gas constituents in the liquid) and desorption (the reverse process of absorption; the gas dissolved in the liquid phase is removed by lowering the partial pressure; if the partial pressure of the material dissolved in the liquid phase is lowered at least partly by passing a carrier gas through the liquid phase, this thermal separating process is also referred to as stripping; alternatively or additionally (simultaneously as a combination), the lowering of the partial pressure can also be brought about by lowering the working pressure).

For example, the removal of (meth)acrylic acid and/or (meth)acrolein from the product gas mixture of the catalytic gas phase oxidation can be conducted in such a way that the (meth)acrylic acid and/or the (meth)acrolein is first subjected to basic removal by absorption into a solvent (e.g. water or an organic solvent) or by fractional condensation of the product gas mixture, and the absorbate or condensate obtained is subsequently separated further to obtain (meth)acrylic acid and/or (meth)acrolein of greater or lesser purity (cf., for example, DE-10332758 A1, DE 10243625 A1, WO 2008/090190 A1, DE 10336386 A1, DE 19924532 A1, DE 19924533 A1, DE 102010001228 A1, WO 2004/035514 A1, EP 1125912 A2, EP 982289 A2, EP 982287 A1 and DE 10218419 A1).

The notation "(meth)acrylic monomers" in this document is an abbreviated form of "acrylic monomers and/or methacrylic monomers".

The term "acrylic monomers" in this document is an abbreviated form of "acrolein, acrylic acid and/or esters of acrylic acid".

The term "methacrylic monomers" in this document is an abbreviated form of "methacrolein, methacrylic acid and/or esters of methacrylic acid".

In particular, the (meth)acrylic monomers addressed in this document shall comprise the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparation of polymers which find use, for example, as adhesives or as water-superabsorbing materials in hygiene articles.

On the industrial scale, (meth)acrolein and (meth)acrylic acid are prepared predominantly by catalytic gas phase oxidation of suitable $C_3/C_4$ precursor compounds (or of precursor compounds thereof). In the case of acrolein and acrylic acid, such precursor compounds used are preferably propene and propane. In the case of methacrylic acid and of methacrolein, isobutene and isobutane are preferred precursor compounds.

As well as propene, propane, isobutene and isobutane, however, suitable starting materials are also other compounds comprising 3 or 4 carbon atoms, for example isobutanol, n-propanol or precursor compounds thereof, for example the methyl ether of isobutanol. Acrylic acid can also be obtained by oxidation of acrolein under gas phase catalysis. Methacrylic acid can also be obtained by oxidation of methacrolein under gas phase catalysis.

In the context of such preparation processes, it is normal to obtain product mixtures from which the (meth)acrylic acid and/or the (meth)acrolein have to be removed.

Esters of (meth)acrylic acid are obtainable, for example, by direct reaction of (meth)acrylic acid and/or (meth)acrolein with the appropriate alcohols. However, in this case too, product mixtures are at first obtained, from which the (meth)acrylic esters have to be removed.

The separating columns in which these separating processes are conducted comprise separating internals. In the thermal separating processes, these have the purpose of increasing the surface area for the heat and mass transfer which brings about the separation in the separating column ("the transfer area").

Useful internals of this kind include, for example, structured packings, random packings and/or trays, which are also referred to as mass transfer trays. Frequently, separating columns used are those which comprise at least one sequence of mass transfer trays as a portion of the separating internals.

The purpose of mass transfer trays is to provide areas having essentially continuous liquid phases in the separating column in the form of liquid layers that form thereon. The surface of the vapor and/or gas stream which ascends within the liquid layer and is distributed in the liquid phase is then the crucial transfer area.

A sequence of mass transfer trays is understood to mean a sequence (a succession) of at least two mass transfer trays generally of the same design (i.e. identical), arranged one above another in the separating column. Advantageously for application purposes, the clear distance between two immediately successive mass transfer trays in such a series (sequence) of mass transfer trays is uniform (meaning that the mass transfer trays are arranged equidistantly one above another in the separating column).

The simplest embodiment of a mass transfer tray is called a trickle sieve tray. This comprises a plate, or plate segments joined to form a plate, having essentially planar passage orifices, for example round holes and/or slots, for the ascending gas or vapor phase (the terms "gaseous" and "vaporous" are used synonymously in this document) distributed over the plate (cf., for example, DE 10230219 A1, EP 1279429 A1, U.S. Pat. No. 3,988,213 and EP 1029573 A1). Any orifices beyond these (for example at least one downcomer (at least one drain segment)) are generally not present in trickle sieve trays. As a result of this absence of downcomers, both the gas ascending within the separating column (the vapor ascending within the separating column) and the liquid descending within the separating column have to move, flowing in opposite directions, alternating in time, through the (same) passage orifices (through the open cross sections of the passages). Reference is also made to the "dual flow" of ascending gas and descending liquid through the passage orifices, which is the reason why the literature frequently also uses the term "dual-flow trays" for mass transfer trays of this type.

The cross section of the passage orifices of a dual-flow tray is matched in a manner known per se to the load thereon. If the cross section is too small, the ascending gas passes through the passage orifices at such a high velocity that the liquid descending within the separating column is entrained essentially without separating action. If the cross section of the passage orifices is too great, ascending gas and descending liquid move past one another essentially without exchange, and the mass transfer tray is at risk of running dry.

In other words, the separation-active working range of a trickle sieve tray (dual-flow tray) has two limits. There has to be a minimum limiting velocity of the ascending gas, in order that a certain liquid layer is held on the trickle sieve tray, in order to enable separation-active working of the trickle sieve tray. The upper limit in the velocity of the ascending gas is fixed by the flood point, when the gas velocity leads to backup of the liquid on the trickle sieve tray and prevents it from trickling through.

The longest dimension of the passage orifices of an industrial dual-flow tray (=longest direct line connecting two points on the outline of the passage orifice cross section) is typically 10 to 80 mm (cf., for example, DE 10156988 A1). Normally, the passage orifices are identical within a trickle sieve tray (in other words, they all have the same geometric shape and the same cross section (the same cross-sectional area)). Appropriately in application terms, the cross-sectional areas are circles. In other words, preferred passage orifices of trickle sieve trays are circular holes. The relative arrangement of the passage orifices of a trickle sieve tray advantageously follows a strict triangular pitch (cf., for example, DE 10230219 A1). It is of course also possible for the passage orifices to be configured differently within one and the same trickle sieve tray (to vary over the trickle sieve tray).

Advantageously in application terms, a sequence of trickle sieve trays comprises trickle sieve trays of the same design (identical trickle sieve trays) in a separating column, preferably arranged equidistantly one above another.

According to DE 10156988 A1, it is also possible to employ sequences of trickle sieve trays in separating columns having a uniform (preferably circular) cross section within a dual-flow tray, but varying within the sequence (for example decreasing from the bottom upward).

In general, each dual-flow tray in a corresponding tray sequence concludes flush with the wall of the separating column. However, there are also embodiments in which an intermediate space interrupted only partly by bridges exists between the column wall and tray. Aside from the actual passage orifices, a trickle sieve tray typically has, at most, orifices which serve to secure the tray on support rings or the like (cf., for example, DE 10159823 A1).

Within the normal working range of a sequence of trickle sieve trays, the liquid descending within the separating column trickles downward in droplets from dual-flow tray to dual-flow tray, meaning that the gas phase ascending between the dual-flow trays is permeated by a divided liquid phase. Some of the droplets that hit the lower trickle sieve tray in each case are atomized. The gas stream flowing through the passage orifices bubbles through the liquid layer formed on the surface of the tray, with intense heat and mass transfer between the liquid and the gas.

According to the gas and liquid load, there is a tendency in trickle sieve trays, in the case of column diameters of >2 m, for slightly unequal distributions of liquids to build up, and thus for the liquid hold-up of a tray to vary over a large area or for a circulating wave to form, which can firstly adversely affect the mechanical stability of the column body and secondly reduces the separating action, since the liquid distribution under these conditions is then time-dependent and highly location-dependent. To avoid such non-steady states, it has therefore been found to be advantageous to distribute baffles in the form of vertical metal sheets over the tray cross section, which prevent or at least greatly reduce buildup of liquid within the column body. The height of the metal sheets should correspond approximately to the height of the liquid froth layer that forms. This is typically about 20 cm at customary loads.

The cross section of a separating column is generally circular. This applies correspondingly to the accompanying mass transfer trays.

Dual-flow trays usable for the purposes of this document are described, for example, in Technische Fortschrittsberichte [Technical Progress Reports], vol. 61, Grundlagen der Dimensionierung von Kolonnenböden [Fundamentals of the Dimensioning of Column Trays], pages 198 to 211, Verlag Theodor Steinkopf, Dresden (1967) and in DE 10230219 A1.

The above-described sequence of trickle sieve trays which comprises mass transfer trays without forced flow of the liquid descending onto the tray on the tray is distinguished from sequences of mass transfer trays with such forced liquid flow.

It is a characteristic feature of these mass transfer trays that they additionally have, as well as the passage orifices already described, at least one downcomer. This is at least one downflow orifice present in the mass transfer tray, toward which the liquid which has descended onto the mass transfer tray (for example over an outlet weir (in the simplest embodiment, this may be an upward extension of the downflow orifice with a neck (a chimney; in the case of a circular downflow orifice, a tube))) flows, and which runs into a shaft which feeds the mass transfer tray below in the sequence and which is generally configured with central symmetry with respect to an axis pointing in the longitudinal direction of the column. The cross section of the shaft may vary (for example narrow) along this axis or else be constant.

By virtue of the at least one downcomer of the mass transfer tray, within a sequence of such mass transfer trays, the liquid descending from a higher mass transfer tray can descend independently of the gas or vapor which continues to rise through the passage orifices of this mass transfer tray as at least one feed of liquid to the next lowest mass transfer tray of the sequence.

The essential basis for this separation of the flow paths of descending liquid and ascending gas is the hydraulic seal (the liquid seal or else shaft seal) of the respective downcomer for the ascending gas (a downcomer must not form a bypass past the passage orifices for the ascending gas; the gas stream (the vapor stream) must not ascend past the passage orifices through a downcomer).

Such a hydraulic seal can be achieved, for example, by drawing the downcomer downward (allowing it to run downward) to such an extent that it is immersed deeply enough into the liquid layer on the next lowest mass transfer tray of the sequence (such a seal is also referred to in this document as "static seal"). The liquid level needed for this purpose can be achieved on the lower mass transfer tray, for example, through the height of appropriate outlet weirs.

However, such a design has the disadvantage that the area of the lower mass transfer tray directly below the outflow cross section of a downcomer of the mass transfer tray above (called the feed area) cannot have any passage orifices for the ascending gas and so is not available for heat and mass transfer between the liquid layer formed on the lower mass transfer tray and the ascending gas.

In an alternative embodiment, the lower outflow end of the downcomer is truncated to such an extent that it is no longer immersed into the liquid layer present on the mass transfer tray below. In this case, between the lower end of the at least one downcomer and the mass transfer tray onto which the downcomer runs, a sufficiently large intermediate space remains, in which a froth layer forms and heat and mass transfer can take place between a liquid layer which accumulates (on the lower mass transfer tray) and a gas ascending (through this tray). In other words, in this case, the "feed area" of the at least one downcomer on the mass transfer tray below may also have passage orifices and can thus increase the available exchange area of the mass transfer tray, and hence the separating action thereof.

A static liquid seal of the downcomer can be brought about in this case, for example, with the aid of a collecting cup mounted below the outflow end of the downcomer. Appropriately in application terms, in this case, the outer wall of the collecting cup is truncated to such an extent that the outflow end of the downcomer is immersed into the collecting cup (it is also possible to allow the lower edge of the downcomer to end at the upper edge of the collecting cup). In the course of operation of the column, the liquid flowing downward through the downcomer collects in the collecting cup until it flows over the upper edge of the outer wall of the collecting cup. The lower edge of the downcomer is immersed into the liquid present in the collecting cup, and the collecting cup forms a siphon-like liquid seal of the downcomer.

Alternatively, a truncated downcomer can also be sealed dynamically. For this purpose, the downcomer can be sealed, for example, at the lower end thereof with a tray provided with exit orifices of such dimensions that the liquid is backed up in the downcomer and prevents the penetration of gas (cf., for example, EP 0882481 A1 and DE 10257915 A1). The shaft seal is established in this case dynamically through the pressure drop which arises at the exit orifices. In other words, in the case of static sealing, the downcomer is sealed by virtue of the outflow end thereof being immersed into backed-up liquid, and, in the case of dynamic sealing, construction features at the outflow end of the downcomer have the effect that the exiting liquid suffers a pressure drop which brings about backup of the liquid descending in the downcomer, which causes the seal. In the simplest case, such a pressure drop can be caused by virtue of a small cross section of the exit orifice of the downcomer being selected compared to the mean cross section of the shaft.

For separation-active operation of a sequence of such mass transfer trays, the design of the at least one downcomer is relevant. Firstly, the cross section of the at least one downcomer selected must be sufficiently large (in general, the corresponding cross-sectional area is greater than the cross-sectional area of a passage orifice), in order that the liquid, even at maximum loading of the separating column, can still descend reliably through the at least one downcomer therewith, and does not back up on the tray above. On the other hand, it has to be ensured that, even in the case of minimal liquid loading, the hydraulic seal of the at least one downcomer still exists.

At a low gas loading, there is likewise the risk of liquid trickling through the passage orifices. In addition, the liquid has to be able to back up in a downcomer to such an extent that the weight of the backed-up liquid column is sufficient to convey the liquid into the gas space below the mass transfer tray to which the downcomer is connected. This backup height determines the required minimum length of the downcomer and thus partly determines the tray separation required in a sequence of corresponding mass transfer trays. A significant partial determining factor for the above backup height (backup length) is the pressure drop $\Delta P$ of a mass transfer tray. This pressure drop is suffered by the ascending gas as it flows through the passage orifices, and the "hydrostatic" head of the froth layer on the mass transfer tray. It is responsible for the fact that the pressure in the gas phase of a sequence of such mass transfer trays increases from the top downward. For the "hydrostatic" pressure $h_p$ of the liquid backed up in the downcomer of a mass transfer tray, it is therefore necessary for at least the condition $h_p > \Delta P$ of the mass transfer tray to be met. These connections are also known to the person skilled in the art, for example, from EP 1704906 A1, as is the possibility of ensuring that, with an inflow weir on the lower mass transfer tray, in the case of static sealing of the downcomer of the upper mass transfer tray in the liquid layer on the lower mass transfer tray, the shaft seal still exists even in the case of low loading with descending liquid. However, the use of an inflow weir increases the backup height required in the downcomer to force the liquid backed up therein onto the lower mass transfer tray. Overall, the element of the downcomer enables a broadening of the separation-active working range compared to the trickle sieve tray. A favorable outflow velocity of the liquid backed up in the downcomer from the downcomer in the process according to the invention is, for example, 1.2 m/s.

In addition, it enables forced circulation of the liquid descending onto a mass transfer tray on this tray.

If, for example, only half of a (preferably circular) mass transfer tray has at least one downcomer (which means that all downflow orifices are present with their full extent within the corresponding circle segment), and, in a sequence of at least two identical mass transfer trays of this kind, the mass transfer trays in a separating column are arranged one on top of another such that two mass transfer trays in the separating column, one of which follows the other in the downward direction, are each mounted offset (turned) by 180° relative to one another about the longitudinal axis of the column, such that the downcomers thereof are on opposite sides (in opposite halves) of the separating column, the liquid which descends from an upper mass transfer tray through the at least one downcomer thereof to the mass transfer tray mounted below must necessarily (i.e. of necessity) flow on this lower mass transfer tray, viewed over the lower mass transfer tray, from the at least one feed area of the at least one downcomer of the upper mass transfer tray (that mounted above) (from the at least one feed through the at least one downcomer of the upper mass transfer tray) to the at least one downcomer of this lower mass transfer tray. In other words, the liquid descending from the upper to the lower tray is inevitably conducted across the tray from the at least one feed to the at least one outlet.

Such a liquid flow on a mass transfer tray within a sequence of identical mass transfer trays shall be referred to in this document as a crossflow, the sequence of such identical mass transfer trays as a sequence of identical crossflow mass transfer trays, and the individual mass transfer trays within the sequence as crossflow mass transfer trays.

In the simplest case, the crossflow mass transfer tray is a crossflow sieve tray. Apart from the at least one downcomer, it has passage orifices for the gas ascending in a separating column, and useful embodiments for the configuration thereof are in principle all of those addressed for the trickle sieve tray. A crossflow sieve tray preferably likewise has circular holes as passage orifices, and these likewise, advantageously for application purposes, have a uniform radius. As already mentioned, the at least one downcomer enables the liquid descending in a separating column, in a sequence of crossflow sieve trays, irrespective of the flow path of the vapor ascending in the sequence, to descend (through the passage orifices) from a higher crossflow sieve tray to the next lowest crossflow sieve tray. On the lower tray, the liquid flows in crosscurrent from the at least one feed of the lower tray, which is formed by the at least one outlet of the higher crossflow sieve tray, to the at least one downcomer (to the at least one outlet) of the lower tray, the desired liquid height on the lower crossflow sieve tray being partly ensured, for example, by the height of at least one outlet weir over which the liquid can flow to the at least one downcomer. In addition, the liquid is retained on the crossflow sieve tray by the backup pressure of the vapor ascending in the separating column. If the vapor loading of a crossflow sieve tray, however, falls below a minimum value, the result may be trickling of the liquid through the passage orifices, which reduces the separating action of the crossflow sieve tray and/or leads to the crossflow sieve tray running dry.

This risk of running dry can be counteracted by providing the downflow orifice of the at least one downcomer with an outlet weir and extending the respective passage orifice in the upward direction with a neck (a chimney; in the case of a circular passage orifice, a tube).

Normally mounted over the end of the neck are vapor-deflecting hoods (bubble caps, inverted cups) (these may in the simplest case be placed on with screw connections to the neck (for example at the front and back) and are effectively pulled over the neck), which are immersed into the liquid backed up on the tray. The vapor ascending through the respective passage orifice at first flows through the neck thereof into the accompanying hood, in which it is deflected, in order then, in contrast to the crossflow sieve tray, to flow in parallel to the tray surface from the hood into the liquid backed up thereon (such a "parallel outflow" is generally favorable in processes according to the invention in that it is able to "blow away" undesirably formed polymer particles and thus to bring about a self-cleaning effect). The gas streams (vapor streams) exiting from adjacent hoods, preferably distributed equidistantly over the trays, agitate the liquid backed up on the tray and form a froth layer therein, in which the heat and mass transfer takes place. Such crossflow mass transfer trays are also referred to as crossflow bubble-cap trays or crossflow hood trays. Since they have backed-up liquid even in the case of low loading with ascending gas (vapor) and thus are at no risk of running dry, they are also referred to as hydraulically sealed crossflow trays. Compared to crossflow sieve trays, they typically require higher capital costs and cause higher pressure drops of the gas ascending through them. The passage orifice of these trays designed (configured) as described is also referred to as bubble-cap passage orifice or hood passage orifice, in contrast to the simple sieve passage orifice of a sieve tray.

The most important component of the crossflow bubble-cap tray is the bubble cap (cf., for example, DE 10243625 A1 and Chemie-Ing.-Techn. Volume 45, 1973/No. 9+10, p. 617 to 620). According to the configuration and arrangement of the bubble caps (vapor deflecting hoods, hoods), crossflow bubble-cap trays are divided, for example, into crossflow round bubble-cap trays (the cross sections of passage orifice, chimney (neck) and bubble cap (vapor deflecting hood) are round (for example the cylinder bubble-cap tray or the flat bubble-cap tray), tunnel crossflow trays (the cross sections of passage orifice, chimney and bubble cap (hood) are rectangular; the passages with their bubble caps are arranged one after another within rows arranged alongside one another, with the longer rectangular edge aligned parallel to the crossflow direction of the liquid) and crossflow Thormann® trays (the cross sections of passage orifice, chimney and bubble cap (hood) are rectangular; the passages with their bubble caps are arranged one after another within rows arranged alongside one another, with the longer rectangular edge aligned at right angles to the crossflow direction of the liquid). Crossflow Thormann trays are described, for example, in DE 19924532 A1 and in DE 10243625 A1, and the prior art acknowledged in these two documents.

Figure 3:
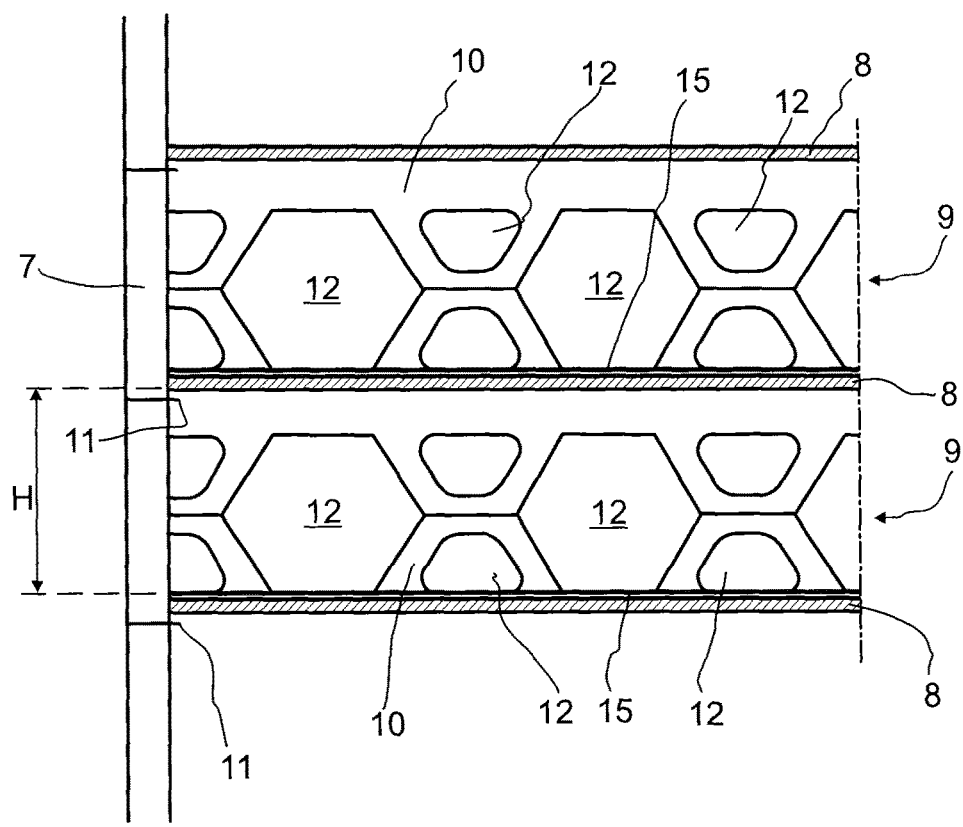

The bubble-cap edge in crossflow bubble-cap trays may have very different forms (cf. DE 10243625 A1 and Chemie-Ing. Techn. Volume 45, 1973/No. 9+10, p. 617 to 620). FIG. 3 from Chemie-Ing. Techn. Volume 45, 1973/No. 9+10, p. 618 shows some examples of the serrated and slotted edge. The serrations and slots are typically shaped such that the vapor emerging from the bubble cap into the liquid backed up on the mass transfer tray dissolves very easily into a large number of bubbles or vapor jets. The above FIG. 3 and various figures in DE 10243625 A1 also show illustrative embodiments of bubble-cap edges having a sawtooth-like structure, the teeth of which are additionally equipped with guide fins (guide surfaces) ("slots bent open"). The guide fins are intended to impose a tangential exit direction on the gas stream (vapor stream) exiting from the sawtooth-like slots bent open (direct the gas exit into the liquid in an oblique direction), as a result of which the surrounding liquid receives a directed movement pulse which, in cooperation with the arrangement of the bubble caps (vapor deflecting hoods), can lead to a directed liquid flow on the crossflow bubble-cap tray, which is superimposed on the crossflow which is established, viewed over the mass transfer tray (frequently, such slots bent open are also referred to as forcing slots). For example, in a sequence of crossflow Thormann trays, the liquid on a lower crossflow Thormann tray does not flow directly across the tray, but rather, in the manner described above, is driven in a meandering manner from the at least one feed to the at least one outlet. The space between two hoods of a crossflow Thormann tray arranged one after the other in crossflow direction forms a channel in each case, in which the liquid flows. The detailed configuration of a crossflow Thormann tray is additionally normally in such a manner that the liquid flows in countercurrent in two channels which are successive in each case in crossflow direction (cf., for example, FIG. 3 of DE 10243625 A1). The meandering crossflow which results in this manner prolongs the flow path of the liquid from the at least one feed to the at least one outlet, which promotes the separating action of a crossflow Thormann tray.

As already stated, in a crossflow bubble-cap tray, the gas emerging from the bubble cap, in contrast to the crossflow sieve tray, is introduced parallel to the tray surface into the liquid backed up on the crossflow bubble cap tray. Frictional and buoyancy forces ensure that, with increasing distance of the emerging gas stream from the bubble-cap edge, more and more substreams thereof are deflected in a direction at right angles to the crossflow bubble-cap tray and ultimately escape from the liquid layer. With increasing gas loading of a bubble cap, the velocity of the gas stream emerging from it grows, which increases the distance from the edge of the bubble cap ("the effective range of the bubble cap") up to which the above-described deflection occurs.

This dependence of the effective range of a rigid bubble-cap on the gas loading can be counteracted by configuring (designing) the passage orifice of a crossflow mass transfer tray as a valve (as a valve passage orifice). The resulting crossflow mass transfer trays are referred to as crossflow valve trays (cf., for example, DD 279822 A1, DD 216633 A1 and DE 102010001228 A1).

The term "crossflow valve trays" in this document thus covers crossflow mass transfer trays which have passage orifices (tray holes) with limited-stroke plate, ballast or lifting valves (floating flaps) which adjust the size of the vapor passage orifice to the respective column loading.

In a simple configuration, the passage orifices of the tray are covered for the aforementioned purpose with covers or plates (disks) movable in the upward direction. In the course of passage of the ascending gas, the lids (plates, disks) are raised by the gas stream in a corresponding guide structure (guide cage) additionally mounted over the respective passage orifice (which is normally firmly anchored on the tray) and finally reach a stroke height corresponding to the gas loading (instead of a guide cage, the disk may also possess upwardly movable valve legs anchored to the tray, the upward mobility of which has an upper limit). The gas stream ascending through the passage orifice is deflected at the underside of the raised lid (plate, disk) in a similar manner to that in the bubble cap (in the case of a bubble-cap passage orifice) and exits from the exit region formed under the raised plate (lid, disk) and, as is the case for the bubble-cap tray, enters the liquid backed up on the tray parallel thereto. The plate stroke thus controls the size of the gas exit region and automatically adjusts to the column loading until the upper end of the guide cage limits the maximum possible stroke height. The plates may have spacers directed downward, such that, at low gas loading, the valve closes only to such an extent that the space provided by the spacers still permits vigorous mixing of the horizontal gas outflow with the crossflowing liquid. Spacers also counteract sticking of the valve disk on the tray. Through suitable configuration of the valve elements of a crossflow valve tray, the blowing direction of the valve element can be adjusted, and hence the forced liquid flow on the crossflow valve tray can additionally be influenced (cf., for example, DD 216 633 A1). The principle of crossflow valve trays, and valve trays usable for the purposes of the present document, can be found, for example, in Technische Fortschrittsberichte, volume 61, Grundlagen der Dimensionierung von Kolonnenböden, pages 96 to 138. As well as the above-described moving valves, the person skilled in the art is also aware of fixed valves. These are normally disk-shaped, or trapezoidal, or rectangular units which are punched out of the tray plate and are connected thereto via fixed legs directed upward.

Especially in the case of relatively large diameters of a separating column, on crossflow mass transfer trays, a notable liquid gradient naturally forms proceeding from the at least one feed until attainment of the outlet weir of the at least one outlet (the gradient of the backup height of the liquid feeds the crossflow (to a limited degree)). The result of this is that, in regions with a relatively low liquid height, due to the resulting lower resistances, the ascending vapor (the ascending gas) can pass through the liquid layer more easily in comparative terms. This can ultimately give rise to an inhomogeneous gas loading of the crossflow mass transfer tray (there is preferential flow through the regions with a lower liquid height (a lower flow resistance)), which impairs the separating action thereof. A compensating effect is possible in this respect through the use of, for example, bubble caps of adjustable height (alternatively, the bubble-cap size can also be altered) in the case of crossflow bubble-cap trays, or by use of, for example, plates (lids) with different weight in the case of crossflow valve trays, such that the mass transfer tray produces gas essentially homogeneously over its cross section (where the liquid height on the crossflow mass transfer tray is lower, the height of the bubble cap is, appropriately in application terms, selected at a correspondingly lower level, or the weight of the stroke plate (stroke lid) is selected at a correspondingly higher level; the height of the bubble cap can, for example, also be lowered by controlled shortening of the length of the corresponding chimney, at the end of which the bubble cap is optionally screwed on; alternatively or additionally, for example, the serration/slot structure of the bubble-cap edge can also be varied in order to bring about the desired flow resistance compensation; ideally, the adjustment is made over the crossflow mass transfer tray such that, in operation of the separating column, every bubble cap present on a crossflow bubble-cap tray causes the same flow resistance for the ascending gas). Otherwise, the passages (the passage orifices) of a crossflow mass transfer tray are generally advantageously configured uniformly.

Orifices running (from the top downward) through a crossflow mass transfer tray, the cross-sectional area of which is typically more than 200 times smaller than the overall cross-sectional area of all other orifices of the crossflow mass transfer tray (not including the cross section of the at least one downcomer), do not constitute (separating) passage orifices for the gas ascending through the crossflow mass transfer tray and are therefore not counted as part thereof. For example, such orifices may be tiny emptying holes through which hydraulically sealed crossflow trays can empty when a separating column is shut down. It is also possible for such orifices to serve for screw connection purposes.

Sequences of mass transfer trays having at least one downcomer, in which the at least one feed and the at least one outlet are present, for example, in the same half of the (circular) mass transfer tray, or in which the at least one feed is in the middle of the tray and the at least one outlet is at the edge of the tray, do not constitute a sequence of crossflow mass transfer trays in the sense of the application (of the invention).

The efficacy of crossflow mass transfer trays designed as described is typically less than that of one theoretical plate (one theoretical separation stage). A theoretical plate (or theoretical separation stage) shall be understood in this document quite generally to mean that spatial unit of a separating column which comprises separating internals and is used for a thermal separation process which brings about enrichment of a substance in accordance with the thermodynamic equilibrium. In other words, the term "theoretical plate" is applicable both to separating columns with mass transfer trays and to separating columns with structured packings and/or random packings.

The prior art recommends the use of sequences of at least two identical crossflow mass transfer trays, in separating columns including those comprising separating internals, which are employed for performance of thermal separation processes between at least one gas stream ascending in the separating column and at least one liquid stream descending in the separating column, and wherein at least one of the streams comprises at least one (meth)acrylic monomer. For example, documents DE 19924532 A1, DE 10243625 A1 and WO 2008/090190 A1 recommend the additional use of a sequence of identical hydraulically sealed crossflow mass transfer trays in a separating column for performance of a process for fractional condensation of a product gas mixture comprising acrylic acid from a heterogeneously catalyzed gas phase partial oxidation of $C_3$ precursors of acrylic acid with molecular oxygen, which comprises, from the bottom upward, at first dual-flow trays and subsequently hydraulically sealed crossflow mass transfer trays.

Figure 4:
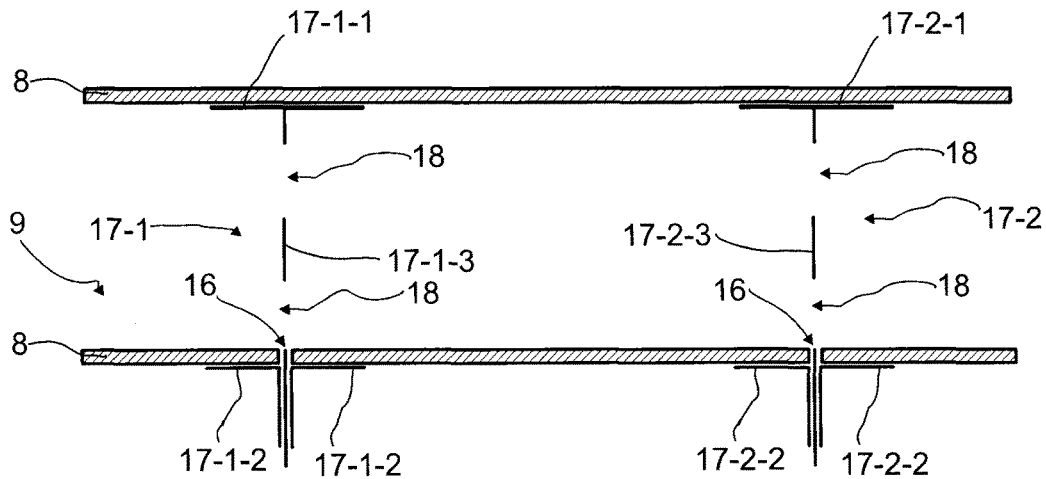

A characteristic feature of the sequences of crossflow mass transfer trays recommended in the prior art is that the lower of two successive crossflow mass transfer trays in the sequence in each case, in the direction of crossflow from the at least one feed thereof to the at least one downcomer thereof, has passage orifices only in the region between the at least one feed and the at least one downcomer (the at least one downflow orifice) (cf., for example, FIGS. 3 and 4 of DE 10243625 A1, FIG. 1 of DD 279822 A1, FIG. 1 of DD 216633 A1, and FIG. 1 from Chemie-Ing.-Techn. Volume 45, 1973/No. 9+10, pages 617 to 620).

The invention relates especially to columns in which the aforementioned trays are used.

Frequently, separating columns for thermal separating processes comprise support elements as a support construction for the trays. WO 2004/092108 A1 describes, for example, a separating column in which the mass transfer trays are supported by a double-T support.

In columns having a very high internal diameter, the problem arises that the trays mounted in the column cavity become unstable. In order to stabilize the trays of column bodies having a diameter greater, for example, than 5 m, support constructions have been used in order to support the trays in vertical direction. However, the problem arose here that thermal treatment of fluid mixtures in the column deteriorated. The separating action was reduced dramatically.

It is therefore an object of the present invention to provide a column of the type specified at the outset, in which the full separation performance is ensured even when the column body has a high diameter. In addition, a tray device for such a column and a thermal separation process between at least one gas ascending within a column and at least one liquid descending within the column are to be specified.

According to the invention, this object is achieved by embodiments according to the claims .

Accordingly, a column has been found for thermal treatment of fluid mixtures, having a cylindrical, vertical column body which forms a column cavity, a plurality of trays mounted with vertical spacing in the column cavity, and a support construction which supports at least one of the trays in vertical direction. It is a characteristic feature of the inventive column that the support construction has a plurality of orifices which allow horizontal mass transfer through the support construction.

In this document, a support construction is understood to mean that the support construction vertically supports at least one tray in the column. The support construction is thus mounted in the column in such a way that it can fulfill the support function. Moreover, the material strengths of the support construction are designed such that the support function can be fulfilled. A support construction is thus, more particularly, not understood to mean baffles which are secured on a tray and which are intended to prevent wave-like stimulation of the liquid present on a tray.

The trays of the column are especially aligned horizontally and mounted with vertical spacing in the column cavity. This forms, for example, a horizontal surface aligned in the downward direction, which is supported by the support construction.

In the case of very high column diameters, it is necessary to use supports having vertical dimensions within the range of the tray spacing. This gives rise to cascaded regions which do not have transverse exchange and in which unequal distributions as a result of crossflows cannot be balanced out sufficiently. In the worst case, there may be formation of regions in which liquid and gas are conducted almost completely separately. It has been found that this effect led to the adverse reduction in separating action at high column diameters.

It has thus been found that the deterioration in the separation performance in the case of a very high column diameter occurs as a result of the support construction preventing mass transfer in horizontal direction in a tray. In such a case, the result is horizontal cascading as a result of the support construction between two vertically adjacent trays. In the inventive column, the support construction has orifices which prevent such cascading, since they allow horizontal mass transfer through the support construction. The result of this was that the disadvantageous effect of the reduction in separation performance in the case of tray supports in which the support height is in the region of the tray spacing no longer occurs.

In a vertical section through the support construction, the orifices take up a proportion of the sectional area of the support construction which is especially within a range from 30% to 90%, preferably within a range from 40% to 80% and more preferably within a range from 50% to 60%. These range figures for the proportion of the orifices in the sectional area of the support construction especially apply to all the vertical sections through the support construction.

It has been found that, especially in the case of the use, as mentioned by way of introduction, of the column for thermal treatment, especially separation, of fluid mixtures, sufficient separating action can only be ensured when sufficient crossflow of the liquid on the tray is possible. In many processes, it is necessary for this purpose that the orifices assume a proportion of the vertical cross-sectional area of the support construction of at least 40%, preferably at least 50%. Depending on the separation process conducted, in the case of large column diameters of more than 5 m, for example, a considerable deterioration in the separating action occurs when the orifices assume a smaller proportion of the vertical cross-sectional area of the support construction.

In a preferred configuration of the column, the support construction has at least one support. The orifices in this case are formed in a vertical wall surface of the support. The support may, for example, be a double-T support, a T support, a U support or a Z support. In that case, the orifices are formed in the vertical wall of the support in each case.

Preferably, the support construction has a plurality of supports, in which case the orifices are also formed in vertical walls of the supports. The supports, spaced apart for example, in horizontal direction, may support a tray in vertical direction.

In one working example of the inventive column, the height of the support(s) corresponds to the vertical distance between adjacent trays, such that the support(s) is/are arranged between adjacent trays. In this way, even in the case of very large column diameters, a stable support construction for the trays is provided.

In one working example of the inventive column, at least some of the orifices are bounded in the downward direction only by an element which rests on the upper face of the tray. The orifices therefore extend very far, as far as the upper face of the tray. In this way, a liquid present on the upper face of a tray can flow virtually unhindered through the support in horizontal direction.

The spatial terms "top", "bottom", "horizontal" and "vertical" relate, unless explicitly stated otherwise, to the orientation of the column during operation.

In another configuration of the inventive column, the support construction is a latticework or framework. A latticework comprises supports consisting of a multitude of rods arranged diagonally and joined to one another at the crossing points to form a lattice. A framework is a construction of a plurality of rods joined to one another at either end. Each rod is part of at least one frame. A frame is thus a polygon consisting of rods. This configuration of the support construction provides very large orifices for particularly good horizontal mass transfer, although the support construction provides adequate stability for the trays even in the case of very high column diameters.

The support construction especially rests on a tray and supports a tray arranged above it from beneath. In this case, it is advantageously unnecessary to secure the support construction itself within the column body. The support construction rests on a lower tray secured within the column body, and in this way supports the tray above it, especially in the region of the middle of the tray. In this way too, a particularly stable construction for the trays can be provided in the column body.

In a further configuration of the column of the invention, in at least a portion of the orifices, the lower boundary edge of the orifice is formed by the tray on which the support construction rests, such that this portion of the orifices allows unhindered horizontal mass transfer along the plane of this tray through the orifices. In the case of these orifices, the support construction is thus open in the downward direction, such that liquid can flow through these orifices on the tray. In this way, particularly good horizontal liquid exchange can be provided on the tray on which the support construction rests.

Alternatively, the lower boundary edge of the orifice is formed not by the tray itself but by an element of the support construction that rests on the top side of the tray. However, this element is only very narrow, such that it only insignificantly impairs horizontal mass transfer on the plane of the tray.

In a further configuration of the inventive column, the support construction has at least one support. This support comprises an upper horizontal limb, a vertical limb and a lower horizontal limb, the upper horizontal limb supporting an upper tray, the vertical limb passing through a lower tray and the latter being supported from beneath by the lower horizontal limb.

The orifices of the support construction in this configuration are formed in the vertical limb. Some of the orifices, especially the lower orifices, may be arranged in the vertical limb such that the lower edge of the orifice is arranged at the level of the upper surface of the lower tray. Through this configuration of the support construction, very good horizontal mass transfer is provided, although the support construction simultaneously has very good stability and can support two trays.

In a development of the column of the invention, at least two orifices are arranged one on top of another with vertical spacing. This means that, at least in some regions, the two orifices arranged one on top of another overlap in the vertical direction. The lateral boundaries of the orifices arranged one on top of another are especially arranged in the same vertical planes. In addition, the shape of the two orifices arranged one on top of another is especially identical. They may optionally be arranged with mirror symmetry. The orifices may, for example, have a trapezoidal shape. This configuration advantageously achieves the effect that mass transfer is assured between two trays in different horizontal planes, while simultaneously maintaining high stability of the support construction.

In a further configuration, the orifices are arranged in at least two horizontal rows with vertical spacing. The orifices of the two horizontal rows may especially be arranged with a horizontal offset from one another. In this way too, mass transfer is enabled in different horizontal planes, at the same time without impairing the stability of the support construction.

In one configuration of the inventive column, the orifices have a honeycomb structure. For example, at least some of the orifices are hexagonal. In this way, it is possible to provide a particularly high stability for the trays, while simultaneously enabling horizontal mass transfer on a tray through the honeycomb structure.

Further separating internals may be disposed in the regions formed between the support(s) and the trays. The separating internals improve the mass separation in a column which is used as a separating column.

These further internals may be provided, for example, in the form of packings, especially structured or ordered packings, and/or beds of random packings. Among the random packings, preference is given to those comprising rings, helices, saddles, Raschig, Intos or Pall rings, Berl or Intalox saddles, Top-Pak etc. Structured packings particularly suitable for extraction columns for use in accordance with the invention are, for example, structured packings from Julius Montz GmbH in D-40705 Hilden, for example the Montz-Pak B1-350 structured packing. Preference is given to using perforated structured packings made from stainless steel sheets. Packed columns having ordered packings are known per se to those skilled in the art and are described, for example, in Chem.-Ing. Tech. 58 (1986) no. 1, pages 19-31 and in the Technische Rundschau Sulzer 2/1979, pages 49 ff. from Gebrüder Sulzer Aktiengesellschaft in Winterthur, Switzerland.

The inventive column can especially be used as a separating column. The separating column has a sequence of trays, especially mass transfer trays. Mass transfer trays used are especially the trays mentioned at the outset, i.e. mass transfer trays without forced flow, such as trickle sieve trays and dual-flow trays, and mass transfer trays with forced liquid flow, for example crossflow mass transfer trays, especially crossflow bubble-cap trays, crossflow hood trays, crossflow Thormann trays and crossflow valve trays.

The clear distance between two immediately successive trays within the inventive column is especially not more than 700 mm, preferably not more than 600 mm or not more than 500 mm. Appropriately in application terms, the clear distance within the tray sequence is 300 to 500 nm. In general, the tray separation should not be less than 250 mm.

In this document, a high diameter of the column body is understood to mean a diameter of at least 5 m. The column body of the inventive column especially has a horizontal maximum extent which is at least 5 m, and especially greater than 5 m, preferably greater than 7 m. If the column body has a circular cross section, the horizontal maximum extent is of the internal diameter of the column body.

The height of the column body is, for example, greater than 5 m, especially greater than 10 m. However, it is also possible for the height of the column body to exceed 30 m or 40 m.

The invention further relates to a tray device for a column for thermal treatment of fluid mixtures, comprising a tray for arrangement in a column cavity of a column and a support construction for the tray having a plurality of orifices which allow mass transfer through the support construction parallel to the tray. If the tray of the tray device is aligned horizontally, for example, in use in the column, the orifices of the support construction enable horizontal mass transfer through the support construction. In the case of use of the tray device in a column, the same advantages can be achieved as in the above-elucidated column.

The invention further relates to a thermal separating process between at least one gas ascending within a column, as described above, and at least one liquid descending within the column. In this case, the ascending gas and/or the descending liquid especially comprises (meth)acrylic monomers.

It has been found that, in the case of a thermal separation process in which the ascending gas or the descending liquid comprises (meth)acrylic acid monomers, mass transfer in the horizontal direction is particularly important. In order to assure sufficient separating action, a particular requirement in this case is that the orifices assume a proportion of the horizontal cross-sectional area of the support construction of greater than 40%, especially greater than 50%.

The thermal separating process according to the invention may, for example, be a process for fractional condensation for separation of acrylic acid from a product gas mixture comprising acrylic acid from a heterogeneously catalyzed gas phase oxidation of a $C_3$ precursor compound (especially propene and/or propane) of the acrylic acid with molecular oxygen to give acrylic acid.

The separating column (condensation column) may be configured as described in documents DE 10243625 A1 and WO 2008/090190 A1, except that the trays used therein are formed by the inventive tray device, i.e. comprise the support construction described.

There follows an elucidation of working examples of the inventive column and working examples of the process according to the invention with reference to the drawings.

Figure 2:
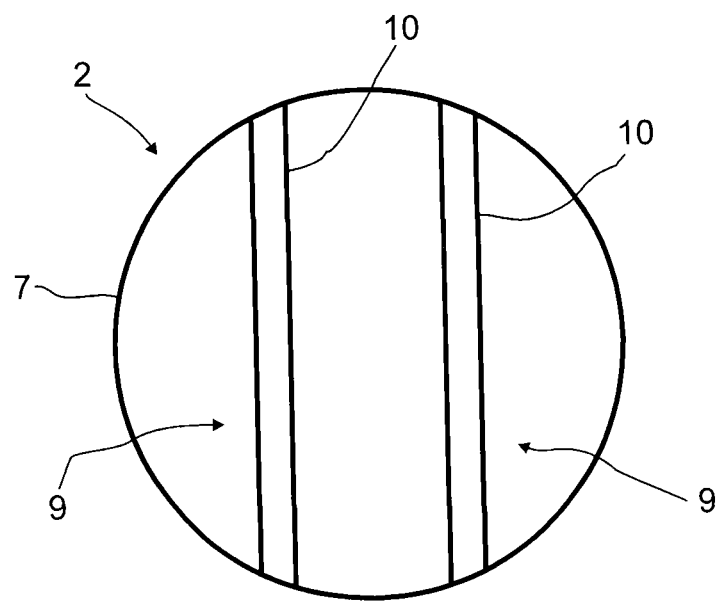
Figure 5:
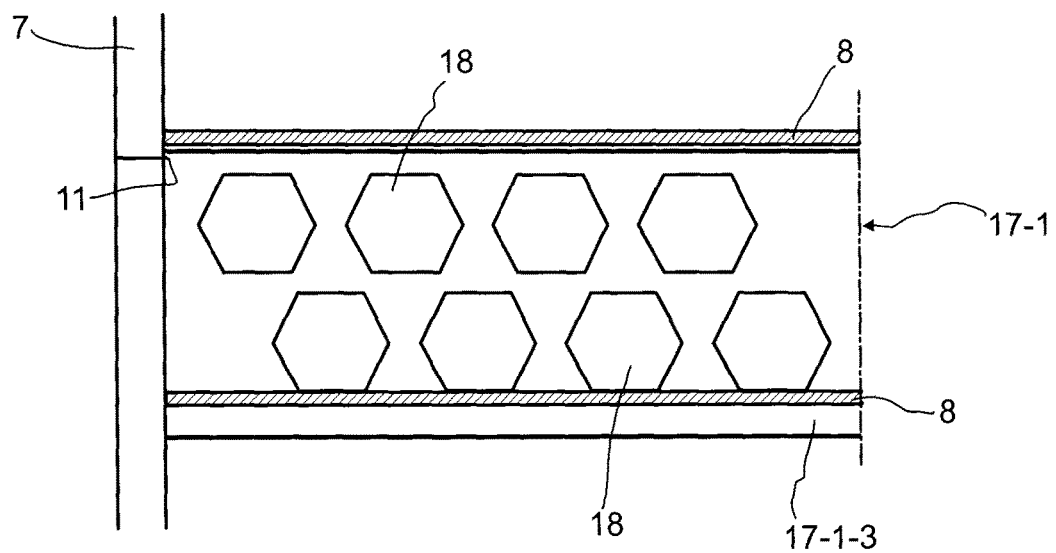

FIG. 1 shows a schematic view of a column in a working example of the invention, FIG. 2 shows a cross section of the column of the working example shown in FIG. 1, FIG. 3 shows a partial view of a vertical section of the column in the working example shown in FIG. 1 with a first example of a support construction, FIG. 4 shows a partial view of a vertical section of the column in the working example shown in FIG. 1 with a second example of a support construction, and FIG. 5 shows a partial view of a vertical section of the column, perpendicular to the vertical section shown in FIG. 4, in the working example shown in FIG. 1 with the second example of the support construction.

The working example described hereinafter relates to a separating column 1 as used, for example, in a process for fractional condensation for separation of acrylic acid from a product gas mixture comprising acrylic acid from a heterogeneously catalyzed gas phase partial oxidation of a $C_3$ precursor compound (especially propene and/or propane) of the acrylic acid with molecular oxygen to give acrylic acid.

FIG. 1 shows the separating column 1 known per se in schematic form. It comprises a cylindrical column body 2, the axis of which is aligned vertically. The column body 2 is essentially a hollow cylinder. This means that the shell 7 of the column body 2 forms a column cavity 3. The column body 2 is manufactured from stainless steel. On the outside, the separating column 1 is normally thermally insulated in a conventional manner. The height of the separating column 1 is 40 m. The internal diameter of the shell 7 of the column body 2 is 7.4 m throughout.

In the vertical direction, the separating column 1 is divided into three regions: the upper region A is referred to as the column head. At the column head is provided a feed 4 through which a liquid can be introduced into the column cavity 3. In addition, an offgas line 13 for withdrawal of the gaseous mixture is formed at the top.

Beneath the column head, a region B is formed. In this region, the fractional condensation is conducted. A withdrawal line 14 is disposed within this region, through which crude acrylic acid is withdrawn.

Beneath region B, the column bottom is formed in region C. In the column bottom, there is an inlet 5 for introduction of the product gas mixture into the column cavity 3. In addition, there is an outlet 6 for the bottoms liquid in the column bottom.

In region B, a plurality of trays 8 secured in the column cavity 3 are horizontal and vertically spaced apart from one another. The trays 8 serve as separating internals which improve separation in the separating column 1. The trays 8 are trickle sieve trays. It is also possible to use other trays among those mentioned by way of introduction.

FIG. 2 shows a horizontal cross section of the separating column 1 in the region B between two trays 8. In the column cavity 3, within the shell 7 of the column body 2, there is a support construction 9 which supports a tray 8 disposed above it in vertical direction. In the working example shown in FIG. 2, the support construction 9 has two supports 10 spaced apart from one another in horizontal direction. The supports 10 are aligned parallel to one another and extend in longitudinal direction of the support 10 from one side of the shell 7 to the opposite side of this shell 7. The supports 10 may each be double-T supports.

FIG. 3 shows a partial view of a vertical cross section through the separating column 1. This partial view shows a section of the shell 7 and sections of three trays 8 in the region of the shell 7. The trays 8 are supported by projections 11 on the shell 7. However, since the diameter of the column body 2 is very high, the trays 8 require further support, especially in the middle. For this purpose, in accordance with the invention, the support construction 9 is provided, comprising, in the working example described here, the supports 10 recognizable in the section shown in FIG. 3.

The configuration of these supports 10 is illustrated in detail hereinafter:

The support 10 rests on the lower tray 8. The upper face of the support 10, configured in the form of a double-T support, supports the lower face of the tray 8 above it from beneath. The height of the support 10 thus corresponds to the vertical clear distance H between two adjacent trays 8. This clear distance H in the working example is a uniform 400 mm.

The supports 10 have a plurality of orifices 12 in the vertical wall. The orifices 12 form a honeycomb structure. Some of the orifices 12 are hexagonal. The orifices 12 allow horizontal mass transfer through the support construction 9 formed by the supports 10.

At least some of the orifices 12 are bounded from beneath only via an element 15 that rests on the upper face of the tray 8. Some of the orifices 12 thus extend very far, as far as the upper face of the tray 8. In this way, it is possible for a liquid present on the upper face of a tray 8 to flow almost unhindered through the support 10 in horizontal direction.

The honeycomb structure of the supports is configured such that the orifices 12 take up a proportion within a range from about 50% to 60% of the vertical sectional area of the support 10.

As shown in FIG. 3, in this honeycomb structure, at least two trapezoidal orifices 12 are arranged one on top of another with vertical spacing. These orifices 12 are arranged with mirror symmetry with respect to a horizontal mirror axis that runs halfway between the two orifices 12 arranged one on top of another.

In another working example, the support construction 9 is a latticework or a framework. In this case, the orifices in a vertical section through the support construction 9 may take up a proportion of up to 90% of the sectional area of the support construction 9. The latticework or framework may also rest on a tray 8 and support the tray 8 arranged above it from beneath. The latticework or framework may, however, also be secured on the shell 7 beneath a tray 8 and support a tray 8 from beneath, but be spaced apart from the tray beneath.

Internals may optionally be arranged within the orifices 12 or within at least some of the orifices 12. Such internals may be packings, especially structured or ordered packings, and/or random packings.

Yet a further example of the support construction 9 is shown in FIGS. 4 and 5. Two double-T supports 17-1 and 17-2 are used, which are supported by the projections 11 in the region of the shell 7. The supports 17-1 and 17-2 have upper horizontal limbs 17-1-1 and 17-2-1 which support the upper tray 8 from beneath. The supports 17-1 and 17-2 also have vertical limbs 17-1-3 and 17-2-3, which each extend downward from the upper horizontal limbs 17-1-1 and 17-2-1. Provided in the lower tray 8 are slot-like orifices 16 through which the vertical limb 17-1-3 or 17-2-3 of the support 17-1 or of the support 17-2 is conducted. Beneath the lower tray 8, lower horizontal limbs 17-1-2 and 17-2-2 which are provided on the vertical limbs 17-1-3 and 17-2-3 support the lower tray 8 from beneath. The support construction 9 in this case therefore supports two trays 8.

The lower orifices 18 are arranged in the vertical limbs 17-1-3 and 17-2-3 such that the lower edge of the orifice 18 is arranged at the level of the upper surface of the lower tray 8. In this way, a liquid can circulate unhindered on the upper surface of the lower tray 8.

The honeycomb structure of the supports 17-1, 17-2, for example, is formed such that the orifices 18 take up a proportion within a range from about 50% to 60% of the vertical sectional area of the supports 17-1, 17-2.

As shown in FIG. 5, the orifices 18 are arranged in two horizontal rows with vertical spacing. In this case, the orifices 18 of the two horizontal rows are arranged with a horizontal offset from one another.

The above-described support construction 9 together with the trays 8 forms a tray device for a column 1, especially a separating column 1, for thermal treatment of fluid mixtures.

There follows a description of a working example of the process according to the invention which is executed with the above-described separating column 1.

The process is a thermal separating process between at least one gas ascending in the separating column 1 and at least one liquid descending in the separating column 1. The ascending gas and/or the descending liquid especially comprises (meth)acrylic monomers.

In the separation process, a fractional condensation for separation of acrylic acid from a product gas mixture comprising acrylic acid from a heterogeneously catalyzed gas phase partial oxidation of a $C_3$ precursor compound (especially propene and/or propene) of the acrylic acid with molecular oxygen to give acrylic acid is conducted in a separating column 1 comprising separating internals. The separating column comprises, from the bottom upward, first dual-flow trays and then crossflow capped trays, which are supported from beneath as described above. Otherwise, the process is conducted as described in documents DE 19924532 A1, DE 10243625 A1 and WO 2008/090190 A1.

The term "$C_3$ precursor" of acrylic acid encompasses those chemical compounds which are obtainable in a formal sense by reduction of acrylic acid. Known $C_3$ precursors of acrylic acid are, for example, propane, propene and acrolein. However, compounds such as glycerol, propionaldehyde or propionic acid should also be counted among these $C_3$ precursors. Proceeding from these, the heterogeneously catalyzed gas phase partial oxidation with molecular oxygen is at least partly an oxidative dehydrogenation. In the relevant heterogeneously catalyzed gas phase partial oxidations, the $C_3$ precursors of acrylic acid mentioned, generally diluted with inert gases, for example molecular nitrogen, CO, $CO_2$, inert hydrocarbons and/or water vapor, are passed in a mixture with molecular oxygen at elevated temperatures and optionally elevated pressure over transition metal mixed oxide catalysts, and converted oxidatively to a product gas mixture comprising acrylic acid.

Typically, the product gas mixture comprising acrylic acid from a heterogeneously catalyzed gas phase partial oxidation of $C_3$ precursors (e.g. propene) of acrylic acid with molecular oxygen over catalysts in the solid state, based on the total amount of the specified constituents present (therein), has the following contents:

1% to 30% by weight of acrylic acid,
0.05% to 10% by weight of molecular oxygen,
1% to 30% by weight of water,
0% to 5% by weight of acetic acid,
0% to 3% by weight of propionic acid,
0% to 1% by weight of maleic acid and/or maleic anhydride,
0% to 2% by weight of acrolein,
0% to 1% by weight of formaldehyde,
0% to 1% by weight of furfural,
0% to 0.5% by weight of benzaldehyde,
0% to 1% by weight of propene, and
as the remainder, inert gases, for example nitrogen, carbon monoxide, carbon dioxide, methane and/or propane.

The partial gas phase oxidation itself can be performed as described in the prior art. Proceeding from propene, the partial gas phase oxidation can be performed, for example, in two successive oxidation stages, as described, for example, in EP 700 714 A1 and in EP 700 893 A1. It will be appreciated, however, that it is also possible to employ the gas phase partial oxidations cited in DE 19740253 A1 and in DE 19740252 A1.

In general, the temperature of the product gas mixture leaving the partial gas phase oxidation is 150 to 350° C., frequently 200 to 300° C.

Direct cooling and/or indirect cooling cools the hot product gas mixture appropriately at first to a temperature of 100 to 180° C., before it is conducted, for the purpose of fractional condensation, into region C (the bottom) of separating column 1. The operating pressure which exists in the separation column 1 is generally 0.5 to 5 bar, frequently 0.5 to 3 bar and in many cases 1 to 2 bar.

LIST OF REFERENCE NUMERALS 1 column, separating column
2 column body
3 column cavity
4 feed
5 inlet
6 outlet
7 shell
8 trays
9 support construction
10 support
11 projection
12 orifices
13 offgas line
14 withdrawal line
15 element
16 orifice
17-1, 17-2 support
17-1-1, 17-1-2 horizontal limb
17-2-1, 17-2-2 horizontal limb
17-1-3, 17-2-3 vertical limb
18 orifices

The invention claimed is:

1. A column for thermal treatment of fluid mixtures, comprising
   a cylindrical, vertical column body which forms a column cavity,
   a plurality of trays mounted with vertical spacing in the column cavity, wherein each tray concludes flush with a wall of the column, and
   a support construction which supports at least one of the trays in a vertical direction,
   wherein:
   the support construction has a plurality of orifices, wherein the orifices allow horizontal mass transfer through the support construction;
   the orifices are arranged in at least two horizontal rows with vertical spacing, wherein at least two orifices are arranged one on top of another with vertical spacing; and
   the support construction rests on a tray and supports a tray arranged above from beneath.

2. The column according to claim 1, wherein in a vertical section through the support construction the orifices take up a proportion of the sectional area of the support construction within a range from 30% to 90%.

3. The column according to claim 1, wherein in a vertical section through the support construction the orifices take up a proportion of the sectional area of the support construction within a range from 40% to 80%.

4. The column according to claim 1, wherein the support construction has at least one support, and the orifices are formed in a vertical wall face of the at least one support.

5. The column according to claim 4, wherein the height of the at least one support corresponds to the vertical spacing of adjacent trays, such that the at least one support is arranged between adjacent trays.

6. The column according to claim 1, wherein the support construction has a plurality of supports and the orifices are formed in vertical wall faces of the plural supports.

7. The column according to claim 6, wherein the height of the plural supports corresponds to the vertical spacing of adjacent trays, such that the plural supports are arranged between adjacent trays.

8. The column according to claim 1, wherein, in at least a portion of the orifices, the lower boundary edge of the orifice is formed by the tray on which the support construction rests, or an element is formed, such that this portion of the orifices allows essentially unhindered horizontal mass transfer along the plane of this tray through the orifices.

9. The column according to claim 1, wherein the support construction has at least one support comprising an upper horizontal limb, a vertical limb and a lower horizontal limb, the upper horizontal limb supporting an upper tray, the vertical limb passing through a lower tray, and the lower tray being supported from beneath by the lower horizontal limb.

10. The column according to claim 1, wherein the orifices of the two horizontal rows are arranged with a horizontal offset from one another.

11. The column according to claim 1, wherein the orifices have a honeycomb structure.

12. The column according to claim 1, wherein at least some of the orifices are hexagonal.

13. The column according to claim 1, wherein the horizontal maximum extent of the column body is greater than 5 m.

14. A tray device for a column for thermal treatment of fluid mixtures, comprising a tray for arrangement in a column cavity of a column and a support construction for the tray having a plurality of orifices which allow mass transfer through the support construction parallel to the tray,
   wherein:
   the orifices are arranged in at least two horizontal rows with vertical spacing, wherein at least two orifices are arranged one on top of another with vertical spacing; and
   the support construction rests on a tray and supports a tray arranged above from beneath.

* * * * *

UNITED STATES PATENT AND TRADEMARK OFFICE
CERTIFICATE OF CORRECTION

| | |
|---|---|
| PATENT NO. | : 10,413,841 B2 |
| APPLICATION NO. | : 14/816485 |
| DATED | : September 17, 2019 |
| INVENTOR(S) | : Ulrich Hammon et al. |

It is certified that error appears in the above-identified patent and that said Letters Patent is hereby corrected as shown below:

On the Title Page

Page 2, Column 2, item (56) Foreign Patent Documents, Line 9, delete "102 57 916" and insert -- 102 57 915 --

In the Specification

Column 8, Line 18, delete "(the" and insert -- the --

Column 11, Line 62, delete "claims ." and insert -- claims. --

Signed and Sealed this
Twenty-eighth Day of April, 2020

Andrei Iancu
*Director of the United States Patent and Trademark Office*